(12) United States Patent
Wilson (10) Patent No.: US 10,818,421 B2
(45) Date of Patent: Oct. 27, 2020

(54) SYSTEMS AND METHODS FOR CONTROLLING ELECTRIC FIELDS IN A FLUID, GASES AND BACTERIA

(71) Applicant: Enhanced Life Water Solutions, LLC, Spanish Fork, UT (US)

(72) Inventor: Gary D. Wilson, Springville, UT (US)

(*) Notice: Subject to any disclaimer, the term of this patent is extended or adjusted under 35 U.S.C. 154(b) by 556 days.

(21) Appl. No.: 15/063,316

(22) Filed: Mar. 7, 2016

(65) Prior Publication Data

US 2016/0260533 A1    Sep. 8, 2016

Related U.S. Application Data

(60) Provisional application No. 62/128,908, filed on Mar. 5, 2015.

(51) Int. Cl.
| | | |
|---|---|---|
| *H01F 7/20* | (2006.01) | |
| *A61N 2/02* | (2006.01) | |
| *H01F 5/00* | (2006.01) | |
| *C02F 1/48* | (2006.01) | |
| *A61N 1/40* | (2006.01) | |
| *C02F 103/02* | (2006.01) | |

(52) U.S. Cl.
CPC .............. *H01F 7/20* (2013.01); *A61N 2/02* (2013.01); *C02F 1/485* (2013.01); *H01F 5/00* (2013.01); *A61N 1/40* (2013.01); *C02F 2103/023* (2013.01); *C02F 2303/04* (2013.01); *C02F 2303/08* (2013.01); *C02F 2303/20* (2013.01); *C02F 2303/22* (2013.01)

(58) Field of Classification Search
CPC ..... H01F 7/20; H01F 5/00; H01F 3/00; H01F 3/02; H01F 2003/005; H01F 7/202; H01F 5/02; H01F 5/04; H01F 5/06; H01F 2005/022; H01F 2005/027; C02F 1/485; C02F 2103/023; C02F 2303/04; C02F 2303/20; C02F 2303/08; C02F 2303/22; C02F 1/484; C02F 1/48; A61N 2/02; A61N 1/40; B03C 1/002; B03C 1/025; B03C 1/0335; B03C 1/034; B03C 1/035; B03C 1/28; B03C 1/288
See application file for complete search history.

(56) References Cited

U.S. PATENT DOCUMENTS

| | | | | |
|---|---|---|---|---|
| 2,982,888 A | * | 5/1961 | Whearley | H01F 5/02 174/120 R |
| 3,189,857 A | * | 6/1965 | Jones | H01F 5/04 336/198 |
| 3,274,527 A | * | 9/1966 | Robinson | H01F 27/343 336/69 |
| 5,776,334 A | * | 7/1998 | Cho | C02F 1/48 204/155 |

(Continued)

*Primary Examiner* — David C Mellon
(74) *Attorney, Agent, or Firm* — Dax D. Anderson; Kirton McConkie (57) ABSTRACT

An electric and magnetic field inducing device is disclosed. The device comprises a malleable core with notches and electrically conductive windings wrapped around the flexible core around the notches. An insulative coating isolates the windings from the core. The device is wrapped around a conduit with flowing fluid and current passed through the windings to treat the fluid. The device can also be placed around a body part and current passed through the windings to provide health benefits.

1 Claim, 9 Drawing Sheets

(56) References Cited

U.S. PATENT DOCUMENTS

| | | | | |
|---|---|---|---|---|
| 6,087,920 | A | * | 7/2000 | Abramov ............ H01F 17/0033 336/192 |
| 7,256,673 | B2 | * | 8/2007 | Okumura ............. H01F 17/045 336/192 |
| 8,477,033 | B2 | | 7/2013 | Claudatos et al. |
| 2004/0050577 | A1 | * | 3/2004 | Manison ................. A61N 2/02 174/108 |
| 2004/0263307 | A1 | * | 12/2004 | Christopherson ......... H01F 5/02 336/174 |
| 2007/0029261 | A1 | * | 2/2007 | Chew ....................... C02F 1/48 210/695 |

* cited by examiner

SYSTEMS AND METHODS FOR CONTROLLING ELECTRIC FIELDS IN A FLUID, GASES AND BACTERIA

CROSS-REFERENCE TO RELATED APPLICATIONS

This application claims priority to U.S. Provisional Application No. 62/128,908 filed Mar. 5, 2015.

BACKGROUND

The embodiments described herein relate generally to generating electromagnetic and electric fields and exposing fluids, gases, and bacteria to these electromagnetic and electric fields, and more particularly, to a device for generating electromagnetic and electric fields to reduce microorganism levels and align molecules in a fluid or gas.

Fluid flowing through a pipe will result in minerals, molecules, macromolecules and solute becoming misaligned. For example, water flowing through pipes generally results in the formation of scale from precipitates. Removal of scale may require the use of harmful chemicals and biocides to treat associated bacteria. Other devices aimed at solving this problem involve cutting the pipes or physically wrapping a wire around the pipes or uses of electromagnetic and/or multi-vibrational fields, e.g., U.S. Pat. No. 8,477,003.

When it comes to a body, such as a human or animal body, inflammation tends to occur due to improper circulation of body fluids. Conventionally, treatment of circulation or inflammation problems includes the use of pharmaceuticals. However, these pharmaceuticals can wear down other bodily organs, such as the liver.

Therefore, what is needed is a means or device that can help improve fluid flow, lower viscosity, reduce levels of microorganisms, align minerals, molecules, macromolecules and solute in a fluid to result in an enhanced fluid without the use of chemicals.

SUMMARY

An apparatus, system and method for exerting an electric and/or electromagnetic field on a flowing fluid to align minerals, molecules, macromolecules and solute is disclosed and claimed. Aligned material remains dissolved and suspended in solution, rather than forming a precipitate. In one embodiment the device may include a plurality of hosting sites, such as notches about a core, a first layer of rubber tape wrapped around the core from notch to notch, a magnetic wire wrapped around the core on top of the rubber tape, a second layer of rubber tape wrapped around the core on top of the magnetic wire, resulting in the magnetic wire being sandwiched between the two layers of rubber tape, and a power supply wire attached to the magnetic wire, the power supply wire configured to engage with a power supply to provide the device with power. In certain embodiments the wire is wrapped in a single direction around the core in a single direction. The device may conform to the shape of an object to which it is applied because the core may be pliable. When the device is in use, it tends to reduce levels of microorganisms and to align and suspend minerals in the fluid flowing through or positioned within the object.

BRIEF DESCRIPTION OF THE FIGURES

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION

In the following detailed description, numerous details, examples, and embodiments are described. However, it will be clear and apparent to one skilled in the art that the present application is not limited to the embodiments set forth and that the present application can be adapted for any of several applications.

In some embodiments, the present disclosure relates to a device that is used to reduce levels of microorganisms and to align molecules in a fluid. While the device may comprise any suitable component that allows it to function as intended, in some embodiments the device comprises a core, a plurality of wire hosting sites on the core, insulating material, windings made from electrically conductive material, and/or a power supply cord. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device. While the various elements of the disclosed device may be related in the following exemplary fashion, it is not intended to limit the scope or nature of the relationships between the various elements and the following examples are presented as illustrative examples only.

Referring to FIGS. 1-9, a device 1 for performing one or more of generating electromagnetic fields, generating electrical fields, generating magnetic fields, manipulating solute in a solvent, reducing levels of microorganism, and for aligning minerals in a fluid is disclosed. Methods of manufacturing, assembling, constructing, and otherwise building the device 1 are also disclosed. The device 1 can be used in a variety of solutes including aqueous and organic solvents (e.g., gasoline, other petroleum based fluids, inorganic solvents, aqueous solvents, salt water, fresh water, and water-based fluids such as biological systems).

Figure 1A:
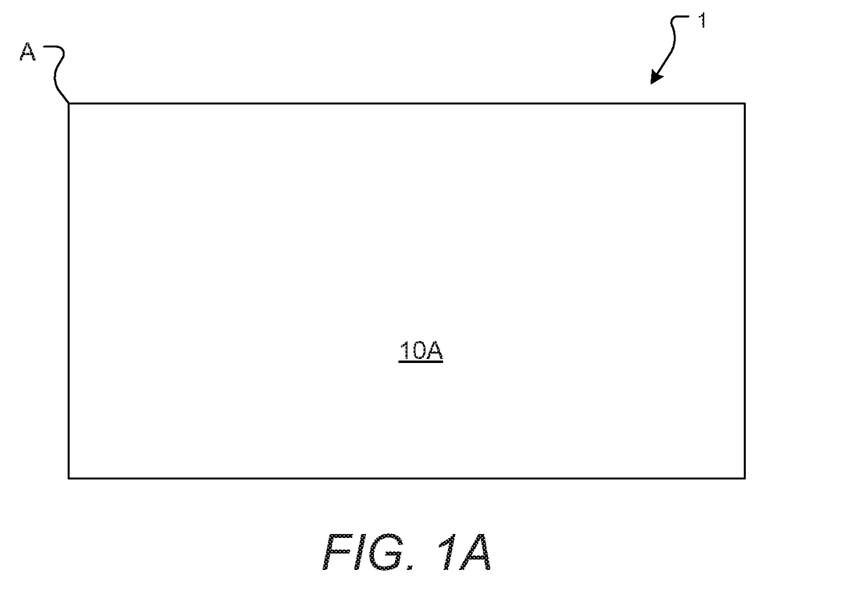
FIG. 1A illustrates a front view of one embodiment of a host for a plurality of wire hosting sites disposed on a flexible core.
Figure 1B:
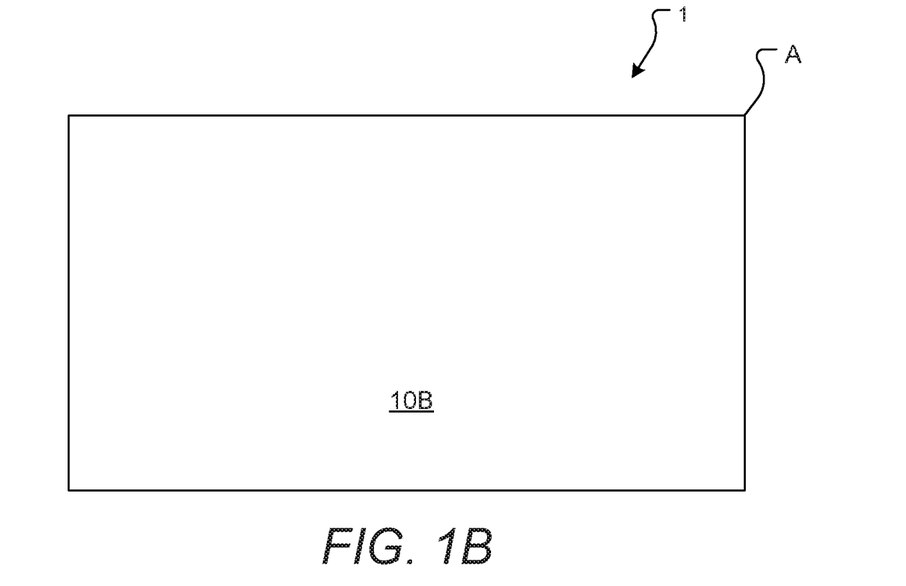
FIG. 1B illustrates a rear view of one embodiment of a host for a plurality of wire hosting sites disposed on a flexible core.

FIGS. 1A and 1B show a substrate or core 10. FIG. 1A shows a front view of the core 10. FIG. 1B shows a rear view of the core 10. Reference A indicates a shared corner between the front view of FIG. 1A and the rear view of FIG. 1B. While the core 10 can comprise any suitable material, in some embodiments, the core 10 comprises a sheet. In other embodiments, the sheet may be pliable. The core 10 may comprise a solid or a mesh. In yet other embodiments, a spacing of the metal mesh is determined by the application. The core 10 may comprise a metal (e.g., a ferrous metal or a non-ferrous metal), a polymer, a composite such as a ceramic, or it may comprise a combination of these materials. The core may comprise a modular system wherein core modules may be selectively coupled to form a core with the desired properties. The core 10 may comprise a flexible sheet metal such as a galvanized sheet metal or a flexible metal mesh. The core 10 can comprise a front 10A and a back 10B.

In some embodiments, the core 10 may comprise a magnetic material which will host or maintain an electrical charge, such as iron. Alternatively, the core 10 may comprise any other desired material, such as a galvanized sheet, wherein the composition of the core 10 may be dependent on the application. In other embodiments, the core 10 may be substantially rectangular. In yet other embodiments, the core 10 comprises any other suitable shape such as substantially round, oval, triangular, or square.

Figure 2A:
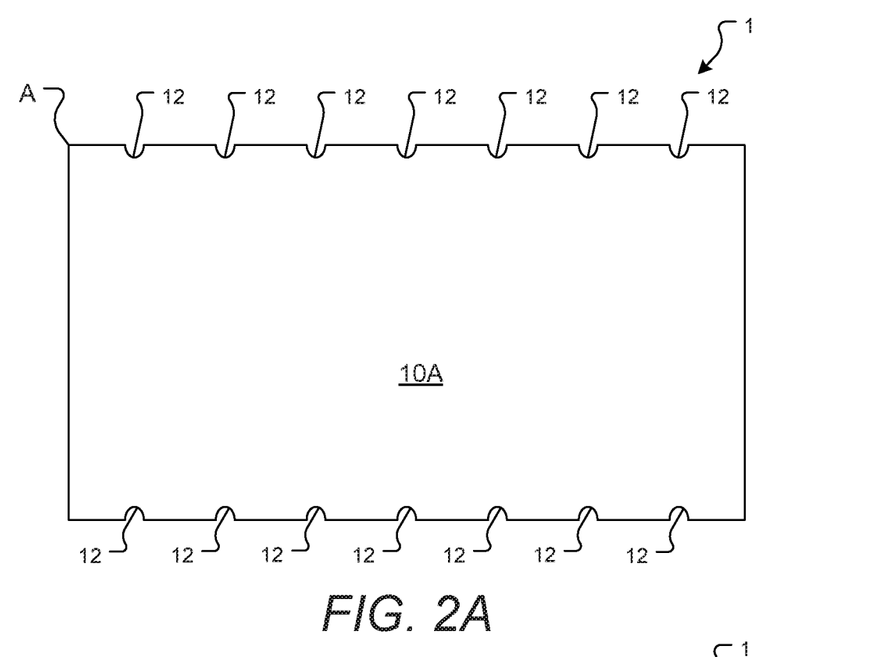
FIG. 2A illustrates a front view of one embodiment of plurality of wire hosting sites in the form of notches in the core of FIGS. 1A and 1B.
Figure 2B:
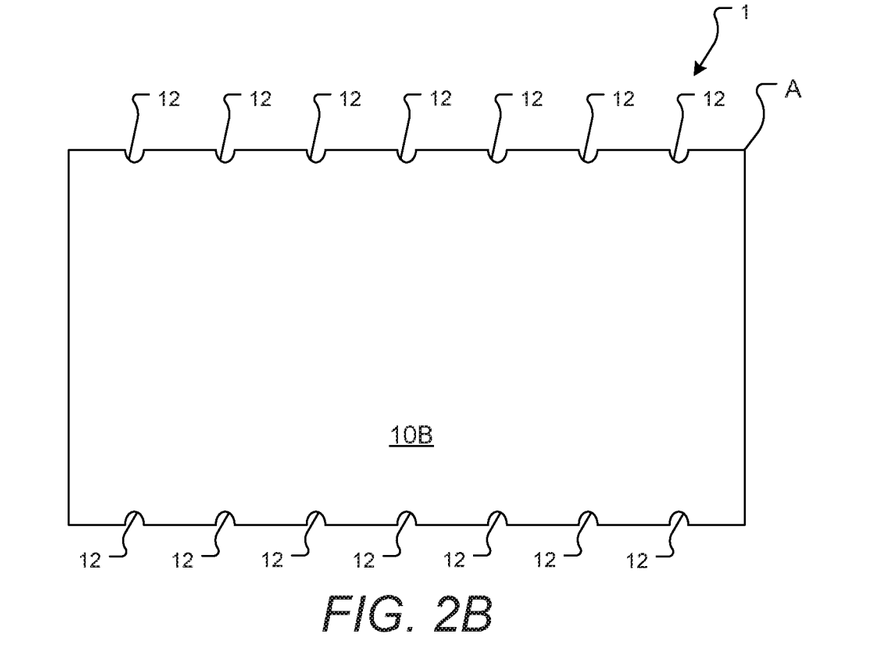
FIG. 2B illustrates a rear view of one embodiment of plurality of wire hosting sites in the form of notches in the core of FIGS. 1 and 1B.

As depicted in FIGS. 2A and 2B, the core 10 may be substantially rectangular and flat having a plurality of hosting sites 12 positioned along a length of two opposing edges of the core 10. FIG. 2A shows a front view of the core 10 with a plurality of notches 12 and FIG. 2B shows a rear view of the core 10 with a plurality of notches 12. Alternative embodiments of the notches 12 may comprise variations of the notches 12 (e.g., protrusions, such as hook, lip, ledge, clip notch recess or other surface feature including welding or soldering sites to which a winding may be secured). Notches 12 may be formed by cutting out or stamping part of core 10 to form notches 12. In an alternative embodiment, hosting sites 12 can be formed by other means such as a mold or other shaping process. The result being, as shown in FIGS. 2A and 2B, that the notches 12 are disposed near opposing sides of the core 10. In certain embodiments the top and bottom edges may comprise notches 12. The notches 12 may be aligned or may be offset. The notches may vary in size or be uniform. The notches may comprise one angle to form V-shape, or may comprise multiple angles. The shape of the notch 12 may be configured to accommodate the gauge of the wire that is used to wrap around the core 10. The notches 12 may be spaced depending on the application, the wire size, the voltage, and the core size. For example, in some embodiments, the notches 12 are spaced from about one half inch to about three inches apart. In alternative embodiments, the notches 12 may be evenly spaced along an edge of the core 10.

Figure 3A:
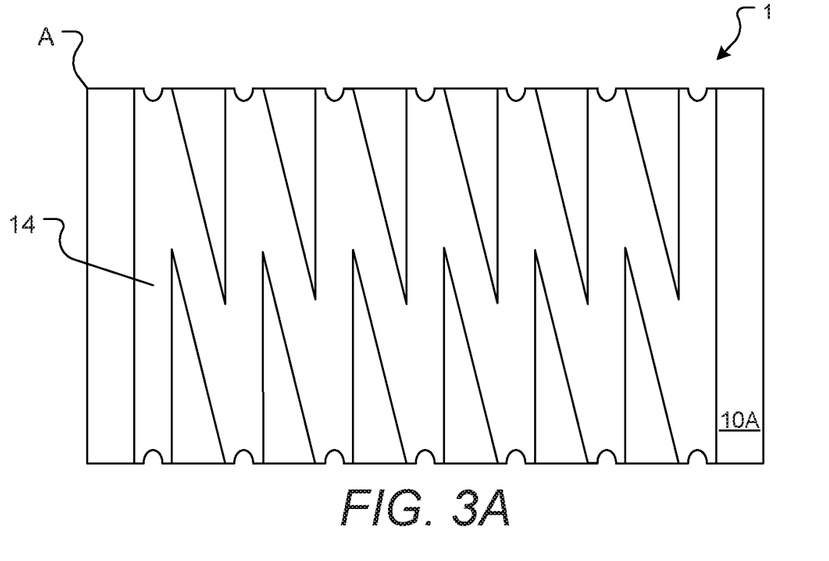
FIG. 3A illustrates a front view of one embodiment of placement of material to protect and isolate wire wrapped or coiled about wire hosting sites.
Figure 3B:
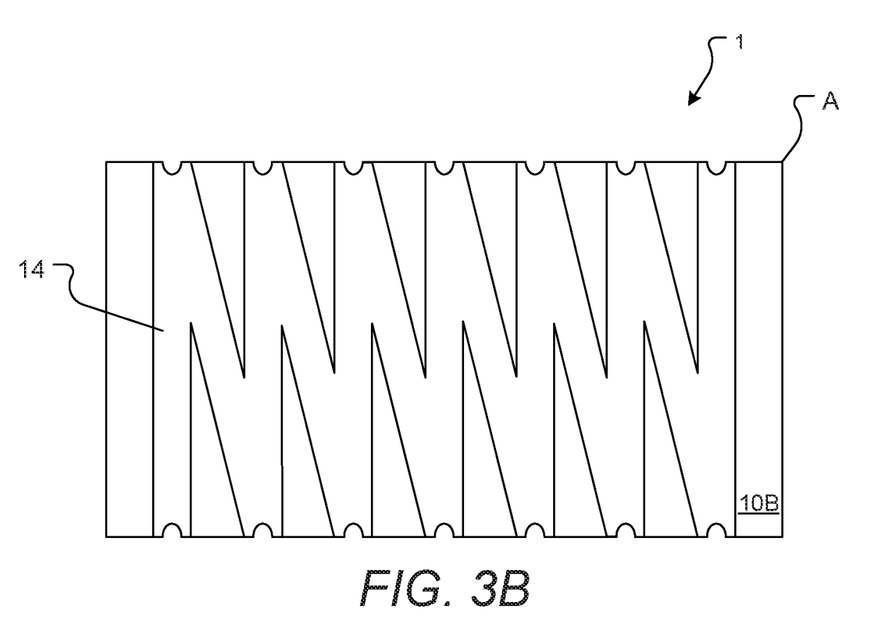
FIG. 3B illustrates a rear view of one embodiment of placement of material to protect and isolate wire wrapped or coiled about wire hosting sites.

Referring now to FIGS. 3A and 3B, the device 1 is shown with a coating 14 applied to the surface of the core 10. FIG. 3A shows a front view of the coating 14 applied to the core 10 and FIG. 3B shows a rear view of the coating 14 applied to the core 10. In some embodiments, the coating 14 is wrapped in a pattern linking a path along the surface of the core between the hosting sites 12. While the coating 14 can comprise any suitable insulating material, in some embodiments, coating 14 comprises any suitable electrical insulation such as insulating rubber tape wrapped around the core 10 from notch 12 to notch 12. The coating 14 may comprise any material comprising insulating qualities (e.g., rubber, plastic, polymer, ceramic, and any other similar insulating material). The coating 14 can be configured as an insulating layer between the wire and the core 10.

In some embodiments, the coating 14 is wrapped from a first notch 12 on a first edge, to a first opposing notch 12 on a second edge, and back up on the first notch 12 on the first edge, and then down diagonally to a second notch 12 on the second edge with this pattern repeated as necessary until the coating 14 has been wrapped through every notch 12. Thus, the applied coating 14 may appear as vertical lines with diagonal lines connecting each vertical line, as shown in the FIGS. The number of times the coating 14 and is wrapped around the core 10 may depend on the application and the size of the core 10.

Figure 4A:
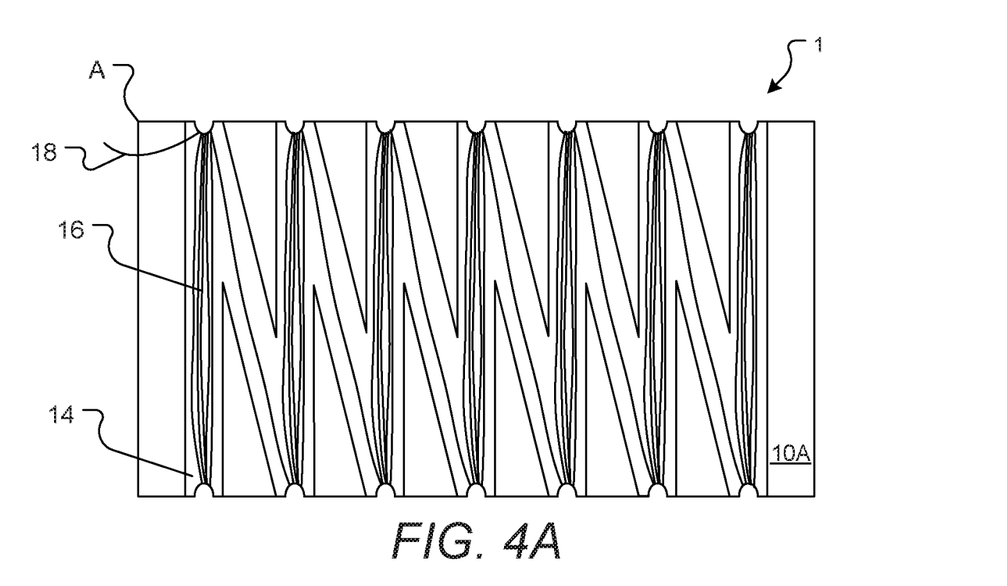
FIG. 4A illustrates a front view of one embodiment of wire coils wrapped about a plurality of wire hosting sites.
Figure 4B:
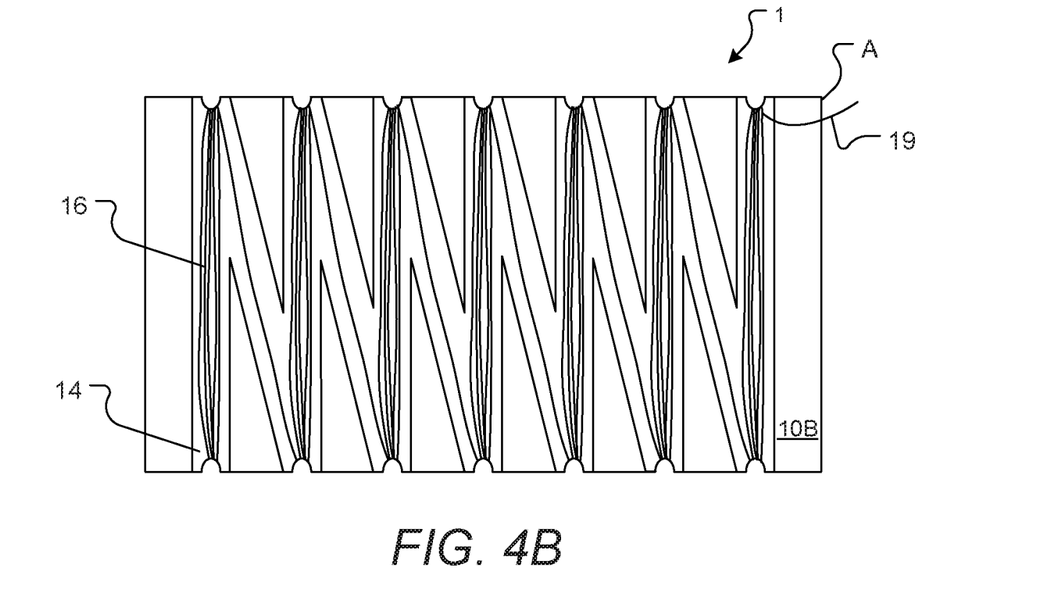
FIG. 4B illustrates a rear view of one embodiment of wire coils wrapped about a plurality of wire hosting sites.

Referring now to FIGS. 4A and 4B, an electrically conductive material can be used to form windings 16. FIG. 4A shows a front view of winding 16 wound onto the coating 14 and FIG. 4B shows a rear view of windings 16 wound onto the coating. The windings 16 can further comprise a first end 18 and a second end 19. The electrically conductive material may comprise wire, carbon nanotubes, single wall carbon nanotubes, polymeric conductors or any other material through which a current can flow to generate an electromagnetic field, an electric field and/or a magnetic field. The windings 16 may be electrical wire such as a copper wire capable of generating an electric field, magnetic field and/or electromagnetic field when electrical power is conducted through windings 16. The windings 16 may comprise stranded wire, non-stranded wire, or any combination of the two. The wire can comprise any suitable or desired electrically conductive or magnetic wire. Depending on the application, the size and composition of the wire may vary.

While the windings 16 can be wrapped around the core 10 in any suitable fashion, in some embodiments, the windings 16 are wound around the core 10 in an orthogonal fashion. Alternatively, windings 16 may be placed completely on one side of the core 10 and secured to the core 10 at two directly opposing hosting sites 12. In some embodiments, the winding 16 is formed by wrapping the electrically conductive material around the core 10 on top of the coating 14 from hosting site 12 to hosting site 12 with the coating 14 disposed between the core 10 and the windings 16. The pattern used to wrap the core 10 may comprise multiple wrappings between opposing notches 12 with a single diagonal wire connecting parallel sets of notches 12. Wires may connect adjacent notches 12 or it may wrap non-adjacent notches 12. For example, the windings 16 can be arranged by winding the electrically conductive material between two directly opposing notches 12 for several windings then making a diagonal transition to an adjacent pair of directly opposing notches 12, wrapping the adjacent pair of directly opposing notches 12, and continuing for the length of the core 10 until the windings 16 are wrapped around each of the notches 12.

A preferred wrapping pattern for the windings 16 may comprise wrapping a wire clockwise around the core between two directly opposing notches five times, then transitioning from the two directly opposing notches across the core 10 in a diagonal direction to the next adjacent pair of opposing notches 12 where the wire is then wrapped between the adjacent pair of opposing notches for five winding and the process continued for a length of the core 10. This pattern of wrapping the wire multiple times between two aligned notches 12, then leading the wire from the bottom notch to the next adjacent top notch in an upward-diagonal pattern where the wire is wrapped around the aligned notches 12 multiple times is repeated until each notch set of aligned hosting sites 12 has a winding with a single wire connecting the adjacent notches on the front side 10A.

The wrapping pattern is continued with the same continuous length of wire with the wrapping pattern repeated from the last winding to the first winding, with the wire used to form windings that overlap the previously placed windings in the same notches where the earlier windings were formed. In stage of the winding, the wire connecting the adjacent notches 12 connects the top notch 12 and extends in a downward diagonal direction to the notch 12 on the bottom edge of the core. The diagonal transition wires on the front of the core 10A and the diagonal transition wires on the back of the core 10B appear to form an "X" although the two wires are on opposite sides of the core 10 and do not touch or physically intersect. In this configuration, current flowing through the windings flows in opposite directions on opposite sides of the core 10.

In some embodiments, the wrapping pattern may comprise wrapping around alternating notches so the wrapping pattern is diagonally offset. Alternatively, the length of the diagonal transition may comprise multiple wrappings or it may be longer to connect wrappings between offset notches. The present disclosure contemplates a core 10 with windings 16 positioned in any suitable fashion along the core. Alternatively, core 10 modules may be formed with windings in place, the core 10 modules being connected consistent with the patterns described herein to allow an electrical current to flow in opposite directions on the front of the core 10A and the back of the core 10B.

In some embodiments, the number of wraps between two aligned notches 12 may vary between 2 wraps and 200 or more wraps. In alternative embodiments the desired number of wraps is completed and the wrapping is continued in the next adjacent notch alignment 12, and as a result, a single wire follows the coating 14 between the two notch alignments 12, and then the wrapping is repeated between the two new notch alignments 12. This pattern is repeated down the length of the core until the wrapping comes to the terminal opposite edge of the core 10, where the same wrapping pattern is repeated along the length of the core 10 in the opposite direction.

As illustrated on the front of core 10A and the back of core 10B in FIGS. 4A and 4B, the wire is wound one or more times between opposing notches 12 to create a wire coil circumscribing the core 10. The wire then passes diagonally across core 10 to the next adjacent opposing notches 12 at which point the wire is again wound one or more times between opposing notches 12 to create another wire coil circumscribing core 10. This wrapping pattern is repeated along the length of core 10 until a coil of wire is disposed between each pair of opposing notches 12 along a length of core 10. This generates a first set of wire coils wrapped around the core 10. When generating the first set of wire coils each diagonal pass of wire 16 to the next adjacent opposing notches 12 can occur on the same side of the core 10 as shown on the front of core 10A as shown in FIG. 4A where a diagonal wire passes diagonally on top of coating 14.

As further illustrated in FIGS. 4A and 4B, after the first set of wire coils is disposed about the core 10, the wire is passed diagonally across the back of the core 10A as shown in FIG. 4B to the next adjacent opposing notches 12 at which point the wire is again wound one or more times between opposing notches 12 to create another wire coil circumscribing the core 10 in the opposite direction. This is repeated along the length of the core 10 until another coil of wire is disposed between each opposing notches 12 along a length of core 10 in an opposing direction. This generates a second or opposing set of wire coils wrapped about the core 10. When generating the second or opposing set of wire coils across the back panel of the core 10B each diagonal pass of wire to the next adjacent opposing notches 12 occurs on the same side of the core as shown for example on the back of the core 10B in FIG. 4B which shows a diagonal transition wire passing diagonally on top of the coating 14. The first set of wire coils and the second or opposing set of wire coils results in the flow of electrical power through the wire in opposing directions between the same two opposing two notches 12.

In some embodiments, the wire is coiled on one side of the core 10 by utilizing two adjacent notches 12 on a same edge around which one end of the coil is wrapped with the other end of the coil being wrapped around two adjacent notches 12 on the opposing edge of the core 10. In other embodiments, posts, hooks or other raised, recessed and/or attached members are disposed on the core 10 to receive and maintain a coil of wire on or about the core 10.

Figure 5A:
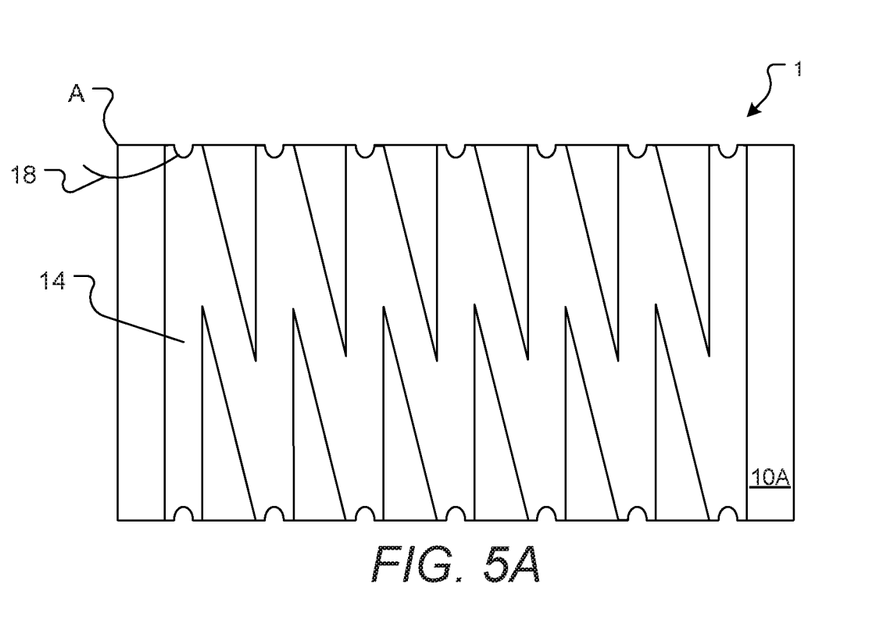
FIG. 5A illustrates a front view of one embodiment of placement of material to protect and isolate wire wrapped about the wire hosting sites.
Figure 5B:
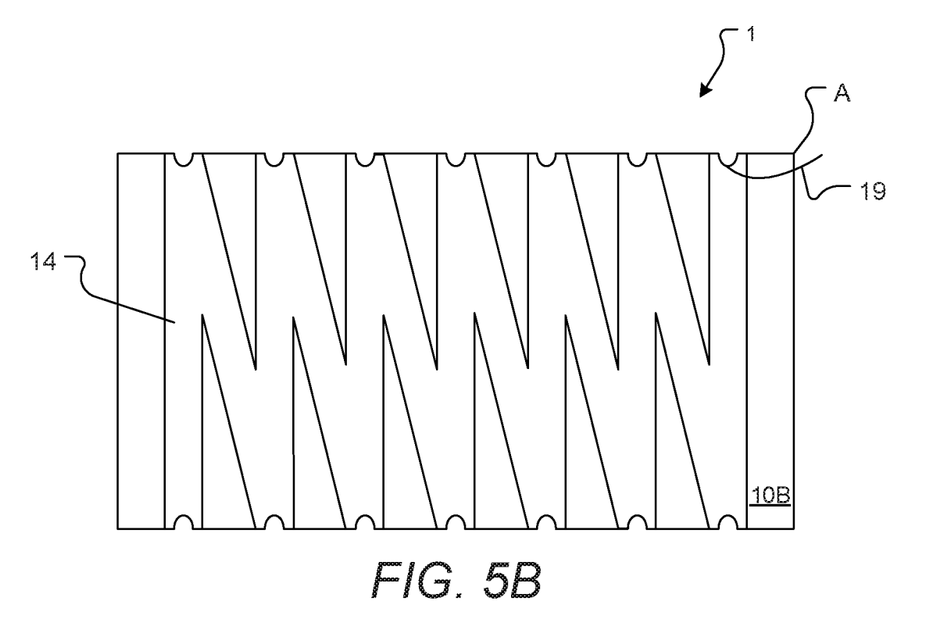
FIG. 5B illustrates a rear view of one embodiment of placement of material to protect and isolate wire wrapped about the wire hosting sites.

Referring now to FIGS. 5A and 5B, a second layer of coating 14 can be applied to the front of the core 10A and the back of the core 10B to cover the windings 16 and the diagonal transitions. FIG. 5A shows a front view of the coating 14 covering the winding 16 and FIG. 4B shows a rear view of the coating 14 covering the windings 16. In some embodiments, the windings 16 are sandwiched between the two layers of coating 14.

Figure 6A:
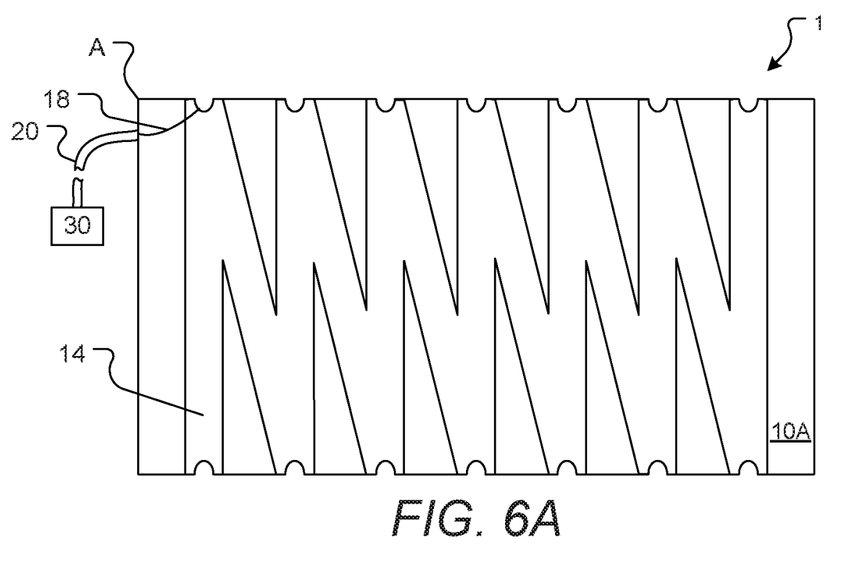
FIG. 6A illustrates a front view of one embodiment of providing electrical connection of the wire wrapped about the plurality of wire hosting sites to a power supply.
Figure 6B:
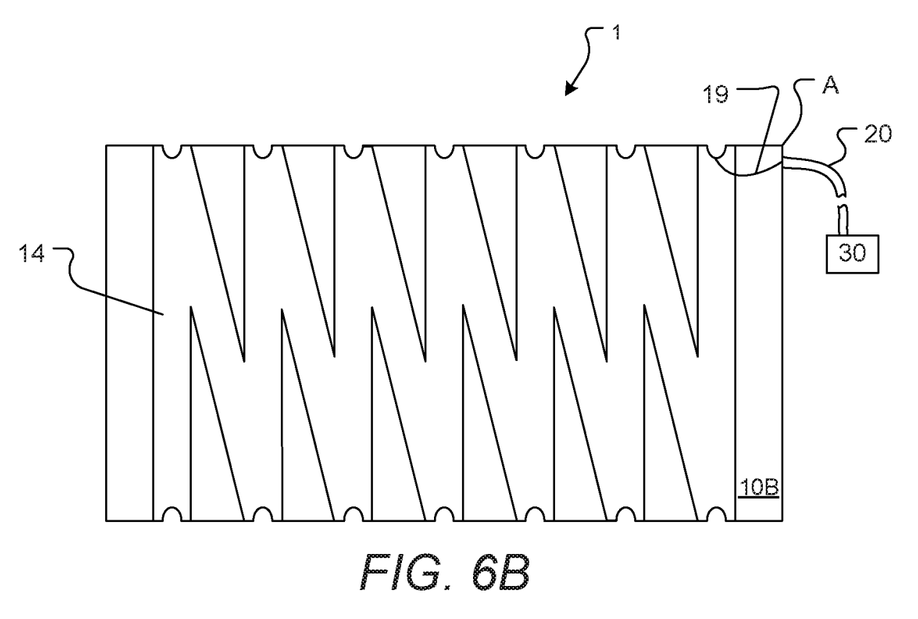
FIG. 6B illustrates a rear view of one embodiment of providing electrical connection of the wire wrapped about the plurality of wire hosting sites to a power supply.

Referring now to FIGS. 6A and 6B, in some embodiments, a power supply wire 20 is attached to the first end 18 and the second end 19 to electrically connect the windings 16 to a power supply 30. The power supply wire 20 can be configured to conduct electrical power from the power supply 30 through the first end 18 and the second end 19 and through the windings 16. The power supply wire 20 may be attached to the first end 18 and the second end 19 using any suitable connection mechanism and, in some embodiments, is soldered to the first end 18 and the second end 19. The power supply wire 20 may comprise any cord configured to engage with the power supply 30 and, in some embodiments, comprises a USB cord or a 21 mm cord, depending on the application. The power supply 30 can comprise a power supply configured to provide a low amount of power, as the system does not require a large amount of power to function. For example, the power supply 30 can comprise a solar power system or any other power system providing from about 3 volts at about 0.1 ampere to about 40 volts at about 15 amperes. In other embodiments, the power supply 30 comprises a power supply providing up to about 1000 volts at up to about 50 amperes.

Figure 7A:
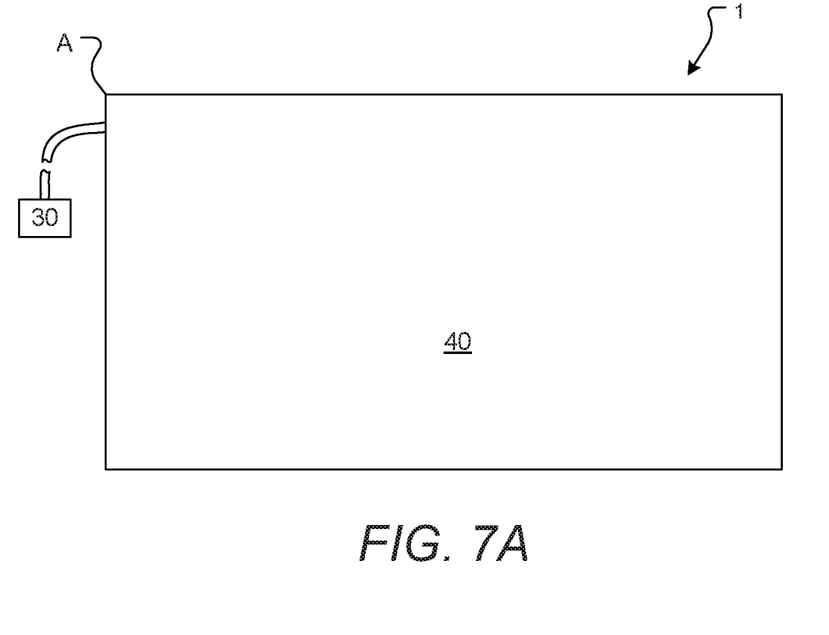
FIG. 7A illustrates a front view of one embodiment of providing a cover to enclose the device.
Figure 7B:
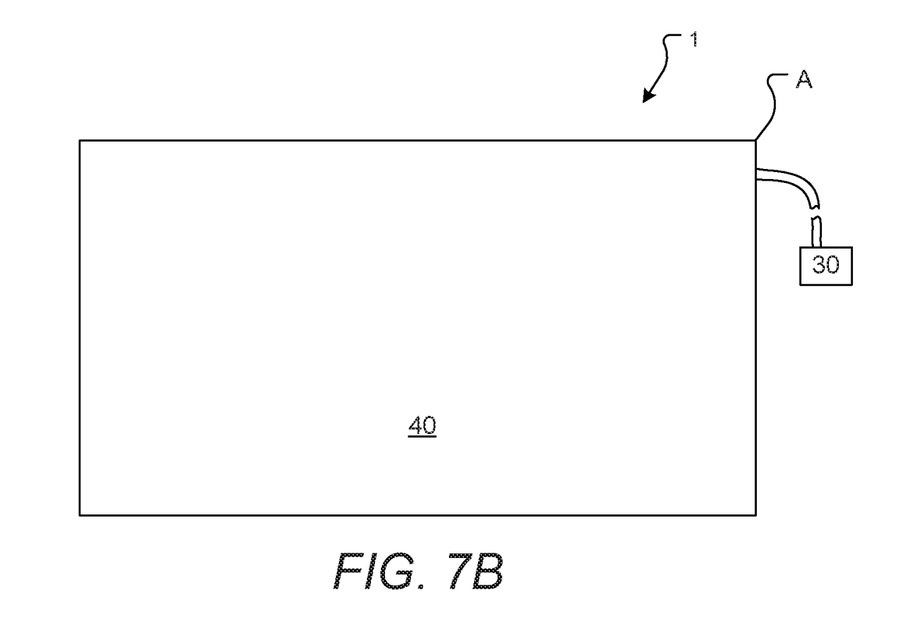
FIG. 7B illustrates a rear view of one embodiment of providing a cover to enclose the device.

Referring now to FIGS. 7A and 7B, in some embodiments the device 1 further comprises a cover 40. FIG. 7A shows a front view of the device 1 with the cover 40 and FIG. 7B shows a rear view of the device 1 with the cover 40. The cover 40 can comprise any suitable material configured to protect the device 1, to electrically insulate the device 1, and/or to prevent a user from contacting the coatings 14, the windings 16, the first end 18, the second end 19, or any other part of the core 10. In some embodiments, the cover 40 comprises a flexible material. The cover 40 may comprise any suitable cover to protect the core. For example, in some embodiments, the cover 40 may comprise a rubberized coating or headliner or any other type of material bonded with adhesive glue, depending on the application.

Without being bound by theory, it is thought that the device functions in configurations that allow competing electric and magnetic fields to interact with sediment in a fluid to reduce the particle size and activate particles suspended in the solution. The reduction in the size of the particulates allows the fluid to flow without creating scaling, blockages or other phenomena that prevent flow, such as in an evaporative cooling system. The activation of the particles prevents the particles from bonding together and precipitating out of solutions. This may result in a super-saturated solution that flows without forming blockages or other obstructions in the system.

In some embodiments, the device functions by adding electrons to the water, other minerals in the water, or whatever substance is in the conduit. In other embodiments, device functions by adding electrons so that the pH is increased by reducing the concentration of Hydrogen Ions (H+). In some cases, the device decreases the concentration of Hydrogen Ions by adding electrons. In other cases, the device adds electrons to substances to change Ca (Calcium) and other minerals to stabilize them. Ca is a positive ion that can be stabilized by introducing additional electrons. The stabilized calcium can resist clumping and stabilize into a particle.

In some embodiments, the device functions by stabilizing all solutions into suspension. In some cases, the device can stabilize molecules into particles that are in suspension instead of solution. By increasing stabilization, a new level of super saturation can be achieved. In other cases, the device can allow the pH to remain stable by employing a focused electron field as a beam-like along the electromagnetic field lines to introduce the electrons into the water, minerals or other substances in the conduit.

In some embodiments, there are two ways that bacteria are affected by the device. The first is that the electron beam or field of electron energy can disrupt the cell membranes of the bacteria and cause the bacteria to die. The second method is by stabilizing the minerals in the water thereby preventing the bacteria from using these mineral. In other embodiments, the device does not affect algae or plants because, as a more complex life form, the algae and plants are able to target the minerals directly for processing by the cells. In some cases, the device can stabilize minerals to promote absorption of the minerals by plants to promote greater and more efficient plant growth.

In some embodiments, the device removes existing hard water deposits. The stabilization effect or crystallization can make the calcium become a particle. In other embodiments, the device changes the water from being a solution to a suspension to allow for super saturation which also can remove existing deposits. In yet other embodiments, the existing deposits become more brittle for solid plate scale cracking during the heating of the bundles. In some embodiments, a granular type of hard water deposit falls off as the calcium is stabilized and no longer binds to metal. In other embodiments, metal is reinforced by the added electrons which prevent corrosion and binding to calcium or other positive ions.

In some embodiments, the device affects the heat energy transfer rate of treated fluids. For example, in water cooling towers, the heat energy given off by towers increases the vibration of the water. That vibration increases until the bonds of the molecules break apart to become vapor by boiling. By adding electrons the device can strengthen the existing bonds so the water does not become vapor as easily. This can allow the water to hold more heat energy thereby increasing the heat energy transfer rate.

In conventional systems, chemicals are used for water treatment to prevent bacteria growth and/or biofouling in the water. With added chemicals in conventional systems, the concentration of hydrogen ions (H+) is high in the acidic range. Although these added chemicals prevents bacteria or other forms of biofouling, acidic water can cause corrosion of pipes and other systems. Therefore, in conventional systems, corrosion inhibitors need to be added to prevent corrosion. In some cases, it can be a delicate balance to get the right amount of added chemicals to prevent biofouling while at the same time preventing corrosion. In some embodiments, the device treats water to control bacterial growth and to reduce and/or prevent biofouling without the need for added chemicals.

In some embodiments, the device functions through the physical phenomena of the electron. The physical phenomena of the electron can be created by electric field lines and directed by electromagnetic fields. When the device is flat it can send out electrons with very little focus. When the device is curved the electromagnetic field can become focused. The physical phenomena can also be called electric permittivity and magnetic permeability. In some cases, electricity can be stopped by resistance (absorbing electrons) while magnetism needs to be redirected for shielding. When the device is in a flat configuration, the device can emit electrons on the positive (magnetic north) side of the core and can absorb electrons from the negative (magnetic south) side of the core. When the device is curved the beneficial effects of the device can be concentrated. The intensity of the electric and magnetic fields can increase as the ends of the core are curved together.

In some embodiments, when the device is curved into a cylinder shape, the electromagnetic field becomes a ring magnet. The directional flow of elections along the magnetic field lines can now move from south to north. The electrons can emit from the north end of the device to create a beam effect. The electric and magnetic field can be intensified by bringing the ends of the core closer together. The directional flow of elections along the magnetic field lines are now moving from south to north. The electrons can emit from the north end of the device to create a beam effect.

In some embodiments, the directional flow of electrons along electric and magnetic field lines creates an electrodynamic energy effect called a focused electron field. In other embodiments, the focused electron field induces molecular stabilization by deionization and recombination from the introduction of an electrodynamic field effect.

In some embodiments, the device provides beneficial health effects when used on a body part. These beneficial health effects can include better absorption of calcium, reduction and/or prevention of kidney stones, decreased viscosity of bloods and/or other bodily fluids, this then increases blood flow, faster healing, better pain management, and dilution of heavy concentration of ions, potential toxins, and improved filtering by the body.

In some embodiments, the device and methods described here are used to improve water softener systems. In some cases, the devices and methods can be used to treat water containing sodium. In other cases, the devices and methods can be used to convert sodium chloride into sodium hydroxide. In yet other cases, the devices and methods can be used to stabilize sodium hydroxide to make it less dangerous. By converting sodium chloride to sodium hydroxide, the device can treat saline water. In some instances, the device and methods can be used to reclaim saline water that was unusable into usable water that can be used for farming or irrigation.

In some embodiments, the overall device may have any desired or required size and may be moldable to mimic the external or internal shape of an object to which it is being applied. In some cases, the device can be configured to be waterproof and/or to be immersed. In other cases, the device can be configured to be oriented within a fluid flow. In general, the device can be used by wrapping around any conduit with flowing fluid. The device can be wrapped such that the windings are parallel to a flow of the fluid. The device is then powered up to generate electric and electromagnetic fields that penetrate the conduct to provide beneficial effects to the flowing fluid. Beneficial effects can include a reduction in the level of microorganisms in the fluid, a reduction and/or a reversal of scale buildup, improved fluid flow, and in the case of application to a body part, improved health benefits.

In some embodiments, the device is applied by wrapping around an object such as a pipe and applying power to the device to cause the minerals and/or precipitates in fluid flowing through the object to align or to be sufficiently suspended in the fluid to prevent scale and other mineral build-up from sticking and/or accumulating to walls, pipes, or other equipment in contact with the fluid. In other embodiments, the device may be used for water treatment to enhance the flavor of water, replace salt-based water softener systems and/or allow salt-based water softeners to operate at a reduction in the use of salt (e.g., a 50% reduction in the use of salt). In yet other embodiments, the device may break the sodium bonds in water so that treated water can be used for plant growth. In some cases, the device is applied to a body to increase blood flow and reduce inflammation. In other cases, the device reduces bacteria growth in treated fluids.

In some embodiments, the core 10 comprises a flexible material configured to be manipulated to match the exterior shape of a conduit such as a pipe in the flow system. In other embodiments, the core 10 may be substantially flat and may be fitted to the desired size for the intended application such as to be wrapped around a pipe, conduit or grease trap. In yet other embodiments, the core 10 may comprise any material configured to form fit to the shape of an object such as a pipe or a body part.

Figure 8:
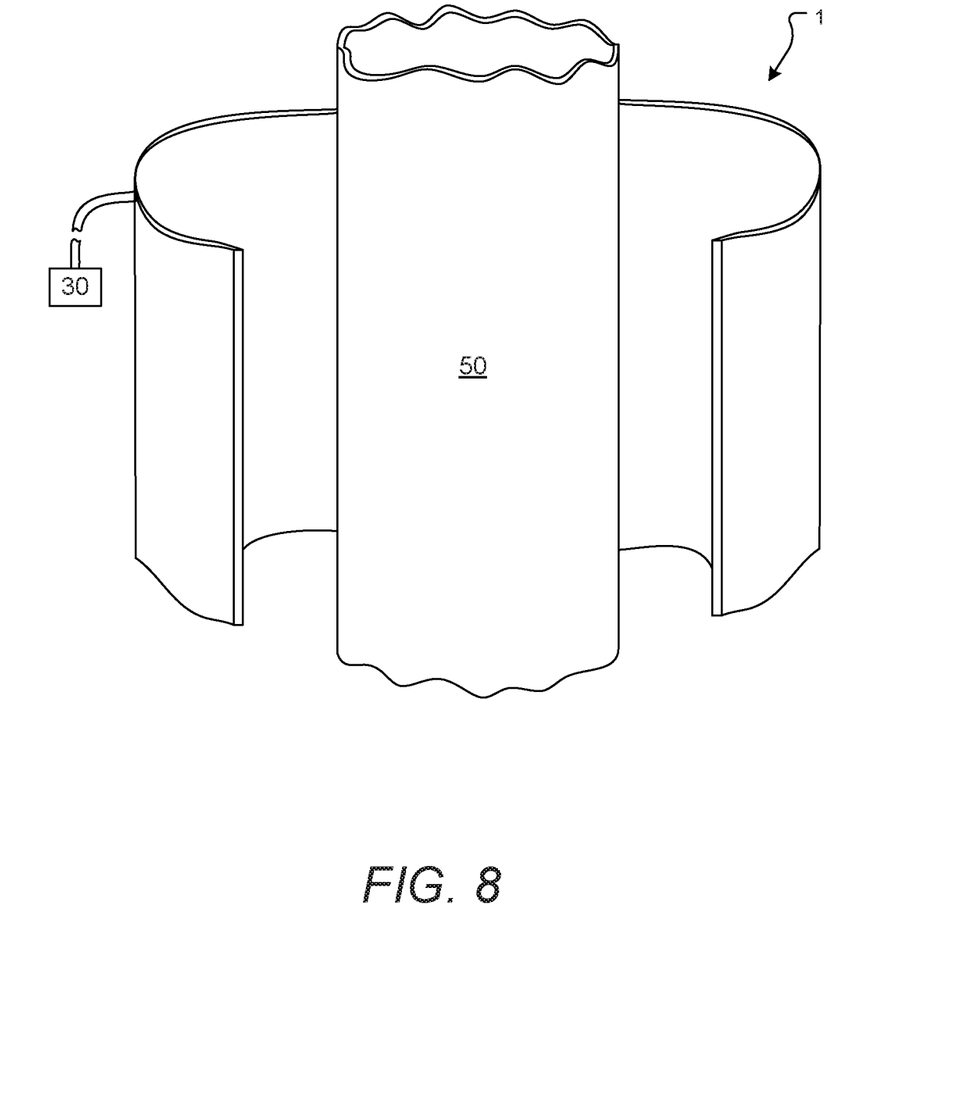
FIG. 8 illustrates one embodiment of placing the assembled device about a conduit for treat of fluid in the conduit.

Referring to FIG. 8, in some embodiments, the device is configured to be flexible to conform to conduits such as pipe. For example, the device 1 can comprise a flexible material configured to be wrapped around a conduit such as a pipe 50. When the device is activated, any fluid flowing through pipe 50 can experience the beneficial effects described above such as, but not limited to, reduced scaling, reduced microorganism levels, and improved fluid flow. In some cases, the device can be configured to wrap around a pipe 50 in a rolled or blanket-like fashion.

Figure 9:
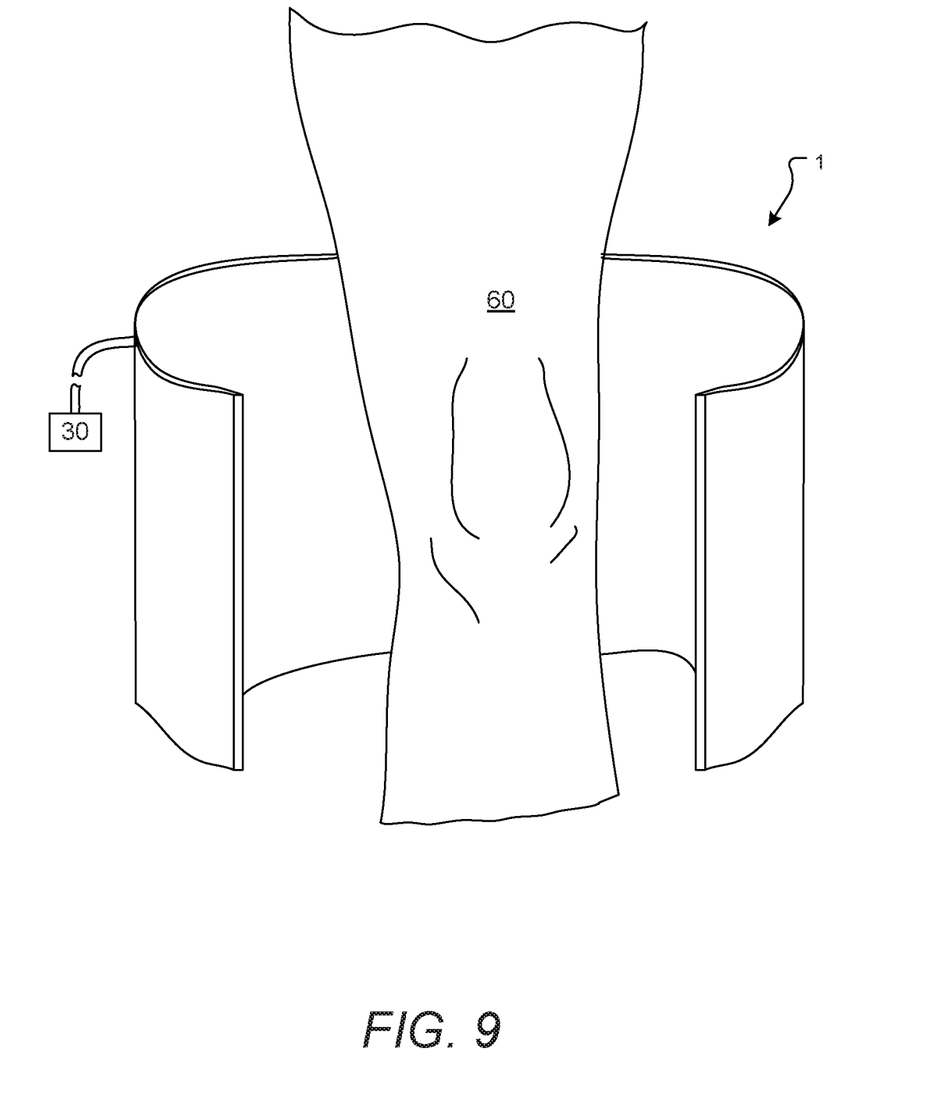
FIG. 9 illustrates one embodiment of placing the assembled device about a body part.

Referring to FIG. 9, in some embodiments, the device is configured as a health pad configured to wrap around a body part such as a knee. For example, the device 1 can comprise a flexible material configured to be wrapped around a body part such as a knee 60. When the device is activated, the wrapped body part can experience the beneficial effects described above such as, but not limited to, reduced inflammation and increase blood flow. In some cases, the device can be configured to wrap around a body part in a rolled or blanket-like fashion. In other cases, body parts can include, but are not limited to toes, feet, ankles, calves, knees, thighs, legs, waists, pelvic areas, abdomen, chest, upper body, shoulders, arms, forearms, hands, necks, or any other suitable body part.

In some embodiments, the disclosed device and methods of use are suitable for any application that requires the treatment of a fluid. For example, the device and methods can be used for health applications in the form of a health pad that is applied different body parts. In some cases, the device and methods can be used for water treatment for one or more of improving water quality, reducing microorganism levels, reducing scaling, and improving water flow. In other cases the devices and methods can be used for fuel treatment for one or more of improving fuel efficiency, improving fuel quality, reducing fuel impurities, and improving combustion. In yet other cases, the devices and methods can be used to assist in filtration of fluids by reducing scaling, improving fluid flow, and/or reducing biofouling. In some instances, the devices and methods can be applied to desalination by reducing scaling, improving water flow, reducing levels of microorganisms, and reducing biofouling. In other instances, the devices and methods can be applied to irrigation to improve water quality, reduce microorganism levels, reduce scaling, and improve water flow. In yet other instances, the devices and methods can be applied to pH adjustment of fluids, hydrogen production, electrolysis, and/or carpet cleaning.

In some embodiments, the present application discloses an electric and magnetic field inducing device comprising a core comprising a sheet having a front side, a back side, a top, a bottom, a first edge, a second edge and a plurality of notches and windings comprising electrically conductive material wrapped around the core, wherein the windings are positioned along the core at the notches, and wherein the windings are in electrical communication to allow current to flow therethrough. In other embodiments, the core comprises a metallic material. In yet other embodiments, the core comprises a ferrous material. In some embodiments, the core comprises a mesh. In other embodiments, the core comprises one or more of a metal, a ceramic, and a polymer. In yet other embodiments, the device further comprises an insulative coating on a surface of the core. In some embodiments, the insulative coating comprises a lower conductance than the electrically conductive material. In other embodiments, the insulative coating is applied to the front and back surfaces of the core in a pattern comprising a plurality of vertical lines connected with diagonal lines. In yet other embodiments, the electrically conductive material comprises wire.

In some embodiments, the device further comprises a first winding formed by wrapping the conductive material around the core a plurality of times in an orthogonal direction at a first set of directly opposing notches, wherein the conductive material is wrapped in a single direction from the front of the core to the back of the core and a second winding formed by wrapping the conductive material around the core a plurality of times in an orthogonal direction at a second set of directly opposing notches, wherein the conductive material is wrapped in a single direction from the front of the core to the back of the core, and wherein the first winding and the second winding are conductively connected.

In some embodiments, the notches comprise protrusions extending from an edge of the core configured so that the conductive material forms a first winding wherein the conductive material is wrapped around a first set of aligned hosting sites so the winding occupies only one surface of the core, wherein the conductive material forms a second winding wherein the conductive material is wrapped around a second set of directly opposed notches so the winding occupies only one surface of the core, and wherein the first winding and the second winding are conductively connected. In other embodiments, the device further comprises a first length of wire disposed about at least two notches by coiling the first length of wire about the two notches in a first direction and a second length of wire disposed about the same two notches by coiling the second length of wire about the same two wire hosting sites in a second direction. In yet other embodiments, the first direction opposes the second direction. In some embodiments, the first length of wire and the second wire are both part of a continuous wire.

In some embodiments, the present application discloses a device for generating electric and magnetic fields, with the device comprising notches, a first wire capable of conducting an electrical current, wherein a first portion of the first wire is disposed about a first set of the notches by coiling the first portion of the first wire about the first set of notches and wherein a second portion of the first wire is disposed about a second set of notches by coiling the second portion of the first wire about the second set of wire hosting sites, and a second wire capable of conducting an electrical current, wherein a first portion of the second wire is disposed about the first set of notches by coiling the first portion of the second wire about the first set of notches in a direction opposing the coiling of the first wire about the first set of notches and wherein a second portion of the second wire disposed about the second set of notches by coiling the second portion of the second wire about the second set of notches in a direction opposing the coiling of the first wire about the second set of notches. In other embodiments, the first wire and the second wire are both part of a continuous wire.

In some embodiments, the present application discloses a method of passing a fluid through an electric and magnetic field comprising providing a core comprising a first set of windings wrapped from a first edge of the core to a second edge of the core and a second set of windings wrapped from the second edge of the core to the first edge of the core, placing the core adjacent to a conduit with fluid flowing therethrough, and applying a current through the windings. In other embodiments, the method further comprises molding the core to the shape of the conduit. In yet other embodiments, the method further comprises wrapping the core around the conduit.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

The invention claimed is:
1. An apparatus for inducing an electric field comprising:
   a ferrous sheet core comprising a plurality of aligned notches on opposite edges of the core;
   a plurality of first bundles of conductive wires wherein a bundle is formed between a set of aligned notches;
   a plurality of front side connecting wires wherein one wire electrically connects one first bundle to another first bundle on the front side of the sheet;
   a plurality of second bundles of conductive wires placed to overlap the first plurality of bundles;
   a plurality of back side connecting wires wherein one wire electrically connects one second bundle to another second bundle;
   wherein the first bundles, the front side connecting wires, the second bundles, and the back side connecting wires are all one continuous wire wound around the core in a single winding direction; and
   wherein the sheet is configured to wrap around a pipe.

* * * * *